(12) United States Patent
Salama

(10) Patent No.: US 7,687,651 B2
(45) Date of Patent: Mar. 30, 2010

(54) METHOD FOR THE PREPARATION OF TRANS-OR CIS-DIAMMONIUMDICHLORO-DIHYDROXOPLATINUM(IV) AND THE USE THEREOF IN THE PRODUCTION OF PHARMACEUTICAL ACTIVE SUBSTANCES

(75) Inventor: Zoser B. Salama, Berlin (DE)

(73) Assignee: RIEMSER Arzneimittel AG (DE)

( * ) Notice: Subject to any disclaimer, the term of this patent is extended or adjusted under 35 U.S.C. 154(b) by 286 days.

(21) Appl. No.: 10/595,400

(22) PCT Filed: Oct. 13, 2004

(86) PCT No.: PCT/DE2004/002296

§ 371 (c)(1),
(2), (4) Date: Feb. 2, 2007

(87) PCT Pub. No.: WO2005/040045

PCT Pub. Date: May 6, 2005

(65) Prior Publication Data

US 2007/0286905 A1 Dec. 13, 2007

Related U.S. Application Data

(60) Provisional application No. 60/512,097, filed on Oct. 20, 2003.

(30) Foreign Application Priority Data

Oct. 13, 2003 (EP) .................. 03090344

(51) Int. Cl.
*C07F 15/00* (2006.01)
*A61K 31/28* (2006.01)
*A61K 33/24* (2006.01)
(52) U.S. Cl. .................. 556/137; 514/492; 424/649
(58) Field of Classification Search .................. 556/137; 514/492; 424/649
See application file for complete search history.

(56) References Cited

U.S. PATENT DOCUMENTS

| 4,394,319 A | * | 7/1983 | Hydes et al. ................. 556/137 |
| 5,196,555 A | * | 3/1993 | Kaplan et al. ................ 556/137 |
| 5,902,826 A | * | 5/1999 | Mogi et al. .................. 514/492 |
| 2007/0048363 A1 | | 3/2007 | Salama |

FOREIGN PATENT DOCUMENTS

| RU | 1137698 | 9/1996 |
| RU | 1021116 | 11/1996 |

OTHER PUBLICATIONS

Hall et al., Journal of Biological Inorganic Chemistry, vol. 8, pp. 726-732 (2003).*
Basler and Groettrup, Drug Aging, vol. 24, No. 3, pp. 197-221 (2007).*
Shore et al., Aliment Pharmacol Ther, vol. 18, pp. 1049-1069 (2003).*
Boulikas et al., Oncology Reports, vol. 10, pp. 1663-1682 (2003).*
PCT/DE2004/002296, International Search Report, Salama, Apr. 15, 2005.
PCT/DE2004/002296, Internat. Search Report, Salama, Apr. 15, 2005.
R.L. Kelland, et al., "Ammin/mine Platinum (IV) dicarboxylates: A novel class of platinum complex exhibiting selective cytotoxicity to intrinsically cis-platin-resistant human ovarian carcinoma cell lines", Cancer Research, vol. 52, No. 4, 1992, pp. 822-828.

* cited by examiner

*Primary Examiner*—Porfirio Nazario Gonzalez
(74) *Attorney, Agent, or Firm*—Joyce von Natzmer; Pequignot & Myers LLC

(57) ABSTRACT

The invention relates to a method for the preparation of trans- or cis-diammoniumdichlorodihydroxoplatinum(IV) and derivatives thereof. What is suggested is reacting trans- or cis-diammoniumdichloroplatinum(II) with a solution comprising >30% peroxide at temperatures below 30° C. and dissolving the product thus obtained in a mineral acid and subsequently precipitating with an alkaline solution.

23 Claims, No Drawings

METHOD FOR THE PREPARATION OF TRANS- OR CIS-DIAMMONIUMDICHLORO-DIHYDROXOPLATINUM(IV) AND THE USE THEREOF IN THE PRODUCTION OF PHARMACEUTICAL ACTIVE SUBSTANCES

This is the U.S. national stage of International application PCT/DE2004/002296, filed Oct. 13, 2004 designating the United States and claiming priority to European application EP03090344.7, filed Oct. 13, 2003 and U.S. provisional application 60/512,097, filed Oct. 20, 2003.

FIELD OF THE INVENTION

The invention relates to a method for the preparation of trans- or cis-diammoniumdichlorodihydroxoplatinum(IV), salts and derivatives derived from said compound; the invention also relates to the use of these compounds in prophylaxis, therapy, follow-up and aftercare of diseases associated with cell growth, cell differentiation and/or cell division, especially tumors.

BACKGROUND OF THE INVENTION

It is well-known that metals such as molybdenum, vanadium, as well as gold and platinum, in particular, can be used in the therapy of acute and chronic diseases such as rheumatism, cancer or autoimmune diseases. Frequently, the metals being used are contacted in the form of complex compounds with the organism to be treated—in many cases via oral ingestion.

The complex compounds comprising the metals are difficult to produce with the required pharmaceutical purity. Numerous production methods which have been described either fail to generate the compounds with sufficient pharmaceutical purity or result in numerous byproducts giving rise to undesirable side effects in the organism. In particular, the preparation of pharmaceutically interesting cis- and trans-oxoplatinum compounds with the required purity or absence of byproducts is not possible with known methods (SU 1137698 A1, SU 1021116 A1). SU 1 137 698 A1 discloses preparation methods for cis-diaminodichlorodihydroxoplatinum(IV). The preparation methods disclosed therein achieve a purity of the final product of 99 to 99.6%.

Furthermore, various acyl derivatives of cis-platinum compounds have been disclosed in the prior art (Kelland et al., Cancer Research, 1992). According to the teaching of Kelland et al., it is the substituents on the nitrogen residue, rather than the acyl residues, that are essential to the effect of these compounds on ovarian cancer cell lines. In the opinion of the authors, there is a close relationship between the substituents on the nitrogen residue and the cytotoxic activity of the compounds. The cytotoxic activity of the cis-platinum compounds increases with increasing amounts of carbon atoms of the substituents on the nitrogen residue. That is, according to the explanations given by Kelland et al., a person skilled in the art would have had no motivation of replacing acyl residues by other moieties, e.g. alkyl residues, because the attention of a person skilled in the art has been drawn to the substituents on the nitrogen residue by Kelland et al. According to Kelland et al., it would make sense to a person skilled in the art to introduce substituents having a preferably large number of carbon atoms as substituent on the nitrogen residue into the respective cis-platinum compounds. According to Kelland et al., ring compounds are particularly advantageous, and a person skilled in the art would therefore be motivated to incorporate other, especially very large, ring compounds in the cis-platinum compounds by means of amine ligand substitution.

The object of the invention was therefore to provide a method allowing easy, reliable and effective provision of cis- or trans-oxoplatinum compounds.

The invention accomplishes the above object by means of a method for the preparation of cis- or trans-diammonium-dichlorodihydroxoplatinum(IV) or diammoniumdichloro-trans-dihydroxoplatinum(IV) and derivatives thereof, wherein cis- or trans-diammoniumdichloroplatinum(II) is reacted with a solution comprising >30% peroxide at temperatures below 30° C., and the product thus obtained is dissolved in a mineral acid and subsequently precipitated with an alkaline solution.

Surprisingly, the combination of features of a solution comprising >30% peroxide and relatively low temperatures, i.e., temperatures below 30° C., allows easy and reliable production of oxo-cis-platinum and oxo-trans-platinum compounds in such a way that small amounts of undesirable by-products are obtained. The method according to the invention utilizes cis- or trans-diammoniumdichloroplatinum(II) compounds as starting compounds, which are converted into the corresponding cis- or trans-form of diammonium-dichloro-trans-dihydroxoplatinum(IV). Advantageously, the solution comprising peroxide is added to the starting compound over a prolonged period of time, preferably in a continuous fashion. The solutions comprising peroxide can be solutions which liberate peroxide during the reaction or behave in a functionally analogous manner due to their specific structure, as is the case with e.g. hydrogen peroxide solutions or perchloroacetic acid solutions.

SUMMARY OF THE INVENTION

In the method according to the invention, high yield and purity of the reaction products are combined with a reaction that proceeds very safely. In contrast to well-known methods, e.g. foaming and spattering of the reaction mixture resulting in loss of platinum is prevented. The high purity of the product obtained allows good further processing into pharmaceutical active substances such as salts and derivatives. Of course, the method according to the invention is also suitable for the production of the desired compounds on a technical or an industrial scale.

In the method according to the invention the starting materials are added repeatedly with hydrogen peroxide solution, especially at high concentration, at low temperatures and optionally with cooling, and reacted for a prolonged period of time, e.g. for several days. By means of the above reaction step it is possible to obtain a solid product, e.g. an initial precipitate which is dissolved by adding a mineral acid. This is followed by precipitation using a preferably concentrated alkali solution.

Thereafter, the product thus obtained can be washed and dried in vacuum.

That is, the product obtained by reacting cis- or trans-diammoniumdichloroplatinum(II) is a solution or a solid, and the product obtained is preferably an initial precipitate. The product obtained is reacted with a mineral acid, e.g. phosphoric acid or sulfuric acid. If the resulting product according to the invention is a precipitate, said precipitate is largely dissolved by means of said mineral acid. The precipitate thus dissolved with mineral acid is subsequently treated with an alkaline solution, e.g. concentrated sodium hydroxide solution, to form a second precipitate. Further work-up of the precipitated cis- or trans-diammoniumdichlorodihydroxoplatinum(IV) depends on the desired further use of the reaction product obtained and is well-known to those skilled in the art.

In a preferred embodiment of the invention the solution comprising peroxide is a highly concentrated hydrogen peroxide solution. Said hydrogen peroxide solution is preferably a >30% hydrogen peroxide solution and more preferably a 35% hydrogen peroxide solution. As is well-known to those skilled in the art, the hydrogen peroxide solution may also include other components increasing the oxidizing effect thereof. For example, the use of a solution of 30% hydrogen peroxide and 70% perchloroacetic acid can be advantageous. Obviously, it is also possible to use a solution which comprises perchloroacetic acid, but no hydrogen peroxide solution. In addition to hydrogen peroxide and perchloroacetic acid, a variety of functionally analogous compounds and solutions generating or providing peroxide, e.g. sodium or potassium peroxide, are known to those skilled in the art.

In another preferred embodiment of the invention the reaction of the diammoniumdichloroplatinum(II), either in the cis- or in the trans-form, with the solution comprising peroxide, preferably hydrogen peroxide solution, is effected at room temperature. Room temperature in the meaning of the invention is between 20° C. and 29° C., preferably between 23° C. and 27° C., and more preferably in a range of from 24° C. to 25° C. As understood herein, however, room temperature is not a fixed temperature range. Depending on other process parameters, the room temperature in the meaning of the invention can also be lower or higher.

In a particularly preferred fashion the reaction of cis- or trans-diammoniumdichloroplatinum(II), or the entire method of the invention, is carried out below 20° C., more preferably below 15° C., even more preferably below 10° C., and particularly below 7° C. Furthermore, it can be particularly preferred to perform the reaction under cooling with ice water so as to achieve a temperature of approximately 4° C. Such cooling, which does not necessarily have to be at 4° C., advantageously suppresses the formation of a number of byproducts.

In another preferred embodiment of the invention, an acid capable of dissolving the product obtained from the reaction of solution comprising peroxide with cis- or trans-diammoniumdichloroplatinum(II) is used as mineral acid, said acid preferably being sulfuric acid. Of course, other mineral acids known to those skilled in the art, such as phosphoric acid, nitric acid, carbonic acid or others, can be used. The required concentration of such mineral acids can easily be determined by a person skilled in the art. Amount and concentration of the above acids should be selected such that the resulting product, in particular, can be dissolved, especially if it is an initial precipitate. Advantageously, the concentration is selected in such a way that only a small amount of mineral acids has to be employed, e.g. a precisely sufficient quantity of 0.5 N sulfuric acid.

In a preferred embodiment of the invention, a sodium hydroxide solution is used as alkaline solution. Advantageously, said sodium hydroxide solution is a 25%, 30%, 33% or 35% sodium hydroxide solution. It is well-known to those skilled in the art that, apart from sodium hydroxide solution, any other basic compound can be used to precipitate the product obtained with the mineral acid. The alkaline solution must be selected such that the final product is as pure as possible and formation of byproducts as low as possible. This can be determined in routine tests by a person skilled in the art.

In another embodiment of the invention, it is preferred to react trans- or cis-diammoniumdichloroplatinum(II) with cooling and repeated addition of the solution comprising peroxide, particularly highly concentrated hydrogen peroxide, over a period of from 12 to 96, preferably from 24 to 48 hours. Here, cooling merely implies that the temperature would not permanently exceed 30° C. Under certain circumstances, however, brief surpassing of this temperature can be possible and desirable. Preferred types of cooling are those which can be accomplished effectively and safely and at low cost on a large scale, e.g. cooling with ice water or ice water/salt mixtures. Cooling is preferably selected in such a way that the highly concentrated hydrogen peroxide solution in particular can be reacted with the starting materials in such a way that a well-controllable chemical reaction would proceed. In the meaning of the invention, controllable means that there would be no vigorous chemical reactions in such a way that e.g. platinum metals would escape from the reaction mixture in the form of splashes or other. Depending on the concentration and selection of the starting materials, the preferred cooling temperature can be a temperature of less than 10° C., more preferably a temperature in a range of from 3° C. to 7° C. By analyzing the purity of the final product and the byproducts possibly present, a person skilled in the art can easily determine whether the entire reaction or merely single partial steps of the reaction should be carried out at the above temperatures. Thus, for example, it can be advantageous to perform only the reaction of the starting materials with the solution comprising peroxide, e.g. hydrogen peroxide solution, at temperatures ranging from 3° C. to 7° C.; however, performing the entire method of the invention within said temperature range can be equally advantageous.

Advantageously, by routinely finding a suitable temperature of less than 30° C. and a corresponding concentration of the solution comprising peroxide, a yield of reaction products of more than 60%, preferably more than 65%, and especially preferably of more than 67% of the theoretically calculated amount of trans- or cis-diammoniumdichlorodihydroxoplatinum(IV) can be achieved in another preferred embodiment of the invention.

The invention also relates to compounds of general formula

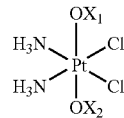

wherein $X_1$, $X_2$=calcium, magnesium, sodium, potassium, lithium, alkyl and/or aryl residues.

The respective compounds of the above general formula may have completely different structures. Thus, if $X_1$ and $X_2$=calcium and/or magnesium, for example, the respective bivalent cations can link two platinum complexes via oxygen molecules, so that two complex compounds are present in associated form. However, if $X_1$ and $X_2$ are sodium or lithium, for example, it is also possible that a compound with only one platinum complex is present. In a preferred fashion, $X_2$ can be a bivalent cation, e.g. calcium or magnesium, linking two complexes each having one platinum central atom, and $X_1$ can be sodium, potassium, lithium, an alkyl and/or aryl residue. Accordingly, it is possible to obtain trans- or cis-diammoniumdichlorodihydroxoplatinum(IV) salts with mono-, bi- or trivalent ions or with mono- and bivalent ions or with mono- and bivalent ions and alkyl and/or aryl residues, each in one single compound, from the base obtained by means of the method according to the invention. Preferred salts are those comprising as cations elements from the main groups I to V or from the subgroups I to VIII of the Periodic Table of the Elements. In a particularly preferred fashion, salts of potassium, lithium, sodium, magnesium, barium, zinc, manganese, silver, copper, vanadium or calcium are used, wherein the anions can be e.g. chlorides, sulfates, phosphates, nitrates or carbonates or others. Other elements capable of forming salts are well-known to those skilled in the art, e.g. all elements from the main groups I to V of the Periodic Table of the Elements, as well as the elements from the subgroups I to VIII; all of the above-mentioned elements of the Periodic Table of the Elements can form cis-oxoplatinum salts. For example, preferred alkyl residues are methyl, ethyl or propyl residues, and preferred aryl residues are phenyl, naphthyl or anthryl residues. The salts and derivatives, especially when generated from the bases produced by means of the method according to the invention, show several advantages compared to cis- or trans-diammoniumdichlorodihydroxoplatinum(IV). Surprisingly, the salts—as compared to the base—have such good solubility that combination with other active substances or vitamins or with other well-known pharmaceutical agents, e.g. anti-tumor agents, is possible with advantage. Surprisingly, in particular, the solubility of the salts according to the invention in 0.1 N HCl is better than that of the corresponding base by many times over. Such a concentration largely corresponds to the concentration of gastric acid, that is, the salts according to the invention will be immediately dissolved in the stomach, especially when reaching the stomach in the form of a pharmaceutical agent via oral ingestion or otherwise. This is particularly advantageous for the treatment of gastric tumors, or to make sure that the compounds of the invention can reach various regions of the organism via absorption in the stomach. The salts and derivatives exhibit higher bioavailability and are more effective at lower dosage than the base from which they are obtained, thereby having less side effects. Also, the residence time of the salts in important metabolic organs such as liver or kidneys is shorter than that of the original compounds. The salts, especially the structures wherein univalent and bivalent cations together form a compound according to the invention, generate less adducts, e.g. in kidneys and liver, and are therefore less nephrotoxic or less toxic to the liver. Furthermore, they are better suited for the gastro-intestinal passage. However, these advantages are not restricted to the salts obtained with mono- and bivalent cations. More specifically, the compounds according to the invention can be employed with advantage in tumor prophylaxis and therapy. Consequently, the invention also relates to the use of the inventive compounds in medicine, especially for the production of a drug.

The compounds according to the invention are contacted with an organism in a therapeutic amount; in this event, the compounds of the invention are employed as pharmaceutical agents or drugs; accordingly, these terms can be used synonymously in the context with this invention. The expression "therapeutic amount" as used herein refers to an amount that prevents or improves symptoms of a disorder or of a responsive, pathologically physiological condition. In specific embodiments of the present invention the amount administered is sufficient to prevent or inhibit a tumor in its growth, said amount essentially prevents or inhibits spreading of a tumor, tumor angiogenesis, tumor invasion and/or tumor metastasizing in a recipient, the tumor diseases being selected from the group of neoplastic tumors, inflammatory tumors and/or abscesses, effusions and edema. As stated above, the invention therefore relates to pharmaceutical agents or drugs comprising the compounds of the invention, optionally together with pharmaceutical adjuvants.

The amount of compounds of the invention to be used in a healthy person in the event of prophylaxis or in a patient in the event of therapy is formulated and the dose established according to conventional medical practice, considering the disorder to be treated, the condition of each individual patient, the site of administration, the procedure of administration and other factors well-known to the attending physicians. Similarly, the dose of the administered compounds of the invention depends on the characteristics of the tumor, on the in vivo half-life of the compounds of the invention in plasma, and on the concentration of the compounds of the invention in the formulation, and also on the route of administration, site and rate of dosage, clinical tolerance of each individual (human and animal), pathological affection of the patient and the like, as is well-known to physicians or other persons skilled in the art. In general, dosages of about 0.1 to 1000 mg per individual and administration are preferred; particularly preferred is a dosage of from 10 to 500 mg, even more preferably 200 to 400 mg, and particularly 300 mg. It is also possible to employ varying dosages during a sequence of consecutive administrations.

For example, injections (intramuscular or subcutaneous or into blood vessels) are envisaged as a route of therapeutic administration of the compounds of the invention, e.g. encapsulated or carrier-bound compounds of the invention, although supply in the form of an aerosol, via catheters or surgical tubes is also applicable. Other preferred routes include suspensions, tablets, capsules and the like for oral administration, commercially available nebulizers for liquid formulations and inhalation of lyophilized or aerolyzed compounds and suppositories for rectal or vaginal administration. Liquid formulations can be solutions, syrups, fluid mixtures, suspensions, emulsions, sterile drug forms (sterile ampoules, septum vials, infusions, lyophilizates) and/or lotions. The suitability of the selected parameters, e.g. dosage, regimen, selection of adjuvants and the like can be determined by taking serum aliquots from the patient, i.e. human or animal, and testing during the course of the applications. Alternatively or concomitantly, the amount of T cells or other cells of the immune system can be determined in a conventional manner so as to obtain an overall survey of the patient's immunologic constitution. In addition, the clinical condition of the patient can be observed for the desired effect. In particular, growth and metastasizing of tumors can be determined. As tumors can be associated with other diseases, e.g. infections, additional co-monitoring of the latter is also possible.

In general, both aqueous formulations and dry compounds of the invention can be mixed with an excipient so as to provide a stabilizing effect prior to treatment e.g. with a solvent. An aqueous solution of a compound according to the invention can be an inventive compound in suspension or a solution. Other forms of preparation, presentation and application are well-known to those skilled in the art, e.g. as a gel, poudrage, powder, tablet, sustained-release tablet, premix, emulsion, brew-up formulation, drops, concentrate, granulate, syrup, pellet, bolus, capsule, aerosol, spray and/or inhalant. The treatment of solid tumors or leukemias comprises prophylaxis, prevention, diagnosis, attenuation, therapy, follow-up and/or aftercare of metastasizing, invasion and/or angiogenesis, said follow-up being monitoring the effectiveness of an anti-tumor treatment.

The compound of the invention can be incorporated in a solution together with a preservative. Examples of suitable preservatives of suspensions or solutions include phenol, benzyl alcohol, m-cresol, methylparaben, propylparaben, benzalkonium chloride and benzethonium chloride. In general, the formulations of the compounds according to the invention may include components in amounts that will not adversely affect the production of stable forms, and in amounts suitable for effective, safe pharmaceutical administration. For example, other pharmaceutically acceptable excipients well-known to those skilled in the art may form part of the compounds or formulations according to the invention. For example, these include salts, various fillers, additional buffer agents, chelating agents, antioxidants, co-solvents and the like.

In a preferred embodiment of the invention the inventive compounds are associated with liposomes, siosomes and/or niosomes.

For example, this can be accomplished in such a way that the compound according to the invention is entrapped in a liposome or anchored on the surface of a liposome. It is well-known to those skilled in the art that artificial or natural membranes of liposomes may have an immune-stimulating effect, especially in those cases where the components are coupled to the surface of liposomes or en-trapped inside the liposomes or simply mixed together with the liposomes. Such formulations of liposomes can be applied on the parenteral route. Using well-known methods, e.g. a spray, such formulations can be applied nasally on the mucosa of the nasal cavity. In a preferred fashion, therapeutic treatment using a spray is suitable for treating lung cancer or tumors in the ear-nose-throat region. Especially in nasal administration, the compound of the invention must be applied on the mucosa in a state permitting penetration of the mucosa or absorption thereby. For this reason, the vesicle must be biocompatible with the mucus and have a certain degree of hydrophilicity. For example, such structures are known to those skilled in the art from EP 0 682 528, the teaching of which is hereby incorporated in the disclosure of the invention. The liposomal composition may comprise one or more additional pharmaceutical carriers selected from surface-active substances and absorption-promoting agents such as polyoxyethylene alcohol ethers, bile salts and derivatives thereof, fusidinic acid and derivatives thereof, oleic acid, lecithin, lysolecithins, Tween® 21 to 85, etc., water-absorbing polymers such as glycofurol, polyethylene glycol 200 to 7500, polyvinylpyrrolidone, propylene glycol or polyacrylic acid, gelatin, cellulose and derivatives etc.; substances inhibiting enzymatic degradation, such as aprotinin etc.; organic solvents such as alcohols, e.g. ethanol, glycerol, benzyl alcohol etc.; or ethyl acetate etc.; hydrophobic agents such as vegetable oil, soybean oil, peanut oil, coconut oil, corn oil, olive oil, sunflower oil, "miglyols" or mixtures thereof, etc.; pH regulators such as nitric acid, phosphoric acid, acetic acid, citrates, etc.; preservatives and agents regulating the osmotic pressure, such as glycerol, sodium chloride, methyl paraoxybenzoate, benzoic acid, etc.; liposomes and/or emulsion formulations such as lecithins etc.; micro-encapsulated formulations; propellants such as butane.

It is preferred in another embodiment of the invention that the compounds according to the invention are optionally associated with each other or, coupled to a carrier, enclosed in liposomes, and such enclosure in liposomes does not necessarily imply—in the meaning of the invention—that the compounds of the invention are present inside the liposomes. Enclosure in the meaning of the invention may also imply that the compounds of the invention are associated with the membrane of the liposomes, e.g. in such a way that the compounds are anchored on the exterior membrane. Such a representation of the inventive compounds in or on liposomes is advantageous in those cases where a person skilled in the art selects the liposomes such that the latter have an immune-stimulating effect. Various ways of modifying the immune-stimulating effect of liposomes are known to those skilled in the art from DE 198 51 282. The lipids can be ordinary lipids, such as esters and amides, or complex lipids, e.g. glycolipids such as cerebrosides or gangliosides, sphingolipids or phospholipids.

In the meaning of the invention, the carriers which can be components of drugs comprising the compounds of the invention can be proteins stimulating an antibody response as a result of their immunogenic behavior, but also pharmaceutical adjuvants well-known to those skilled in the art, such as QS-21, GPI-0100 or other saponines, water-oil emulsions such as Montanides, polylysine, polyarginine compounds, or others, e.g. phosphate-buffered saline, water, various kinds of detergents, sterile solutions and the like.

A pharmaceutical agent in the meaning of the invention is any agent in the field of medicine, which can be used in prophylaxis, diagnosis, therapy, follow-up or aftercare of patients comprising a tumor in such a way that a pathogenic modification of their overall condition or of the condition of particular regions of the organism could establish at least temporarily. Thus, for example, the pharmaceutical agent in the meaning of the invention can be a vaccine or a therapeutic agent. In addition to the compounds of the invention, the pharmaceutical agent in the meaning of the invention may include e.g. an acceptable salt or components thereof. For example, these can be salts of inorganic acids such as phosphoric acid or salts of organic acids.

Furthermore, the salts can be free of carboxyl groups and derived from inorganic bases such as sodium, potassium, ammonium, calcium or iron hydroxides, or from organic bases such as isopropylamine, trimethylamine, 2-ethylaminoethanol, histidine and others. Examples of liquid carriers are sterile aqueous solutions including no further materials or active ingredients, e.g. water, or those comprising a buffer such as sodium phosphate with a physiological pH or a physiological salt solution or both, such as phosphate-buffered sodium chloride solution. Other liquid carriers may comprise more than just one buffer salt, e.g. sodium and potassium chlorides, dextrose, propylene glycol, polyethylene glycol, or others. Liquid compositions of the pharmaceutical agents may additionally comprise a liquid phase, with water being excluded, however. Examples of such additional liquid phases are glycerol, vegetable oils, organic esters or water-oil emulsions. The pharmaceutical composition or pharmaceutical agent typically includes a content of at least 0.1 wt.-% of compounds according to the invention, relative to the overall pharmaceutical composition. The respective dose or dosage range for administering the pharmaceutical agent according to the invention is sufficiently high or wide in order to achieve the desired prophylactic or therapeutic effect of forming neutralizing antibodies. In this context, the dose should not be selected in such a way that undesirable side effects would dominate. In general, the dose will vary with the patient's age, constitution, sex and, of course, depending on the severity of the disease. The individual dose can be adjusted both with reference to the primary disease and with reference to the occurrence of additional complications. Using well-known means and methods, the exact dose can be determined by a person skilled in the art, e.g. by determining the tumor growth as a function of dosage or as a function of the application regime or pharmaceutical carrier and the like. Depending on the patient, the dose can be selected individually. For example, a dose of pharmaceutical agent just tolerated by a patient can be such that the range thereof in plasma or locally in particular organs is from 0.1 to 10,000 µM, preferably between 1 and 100 µM. Alternatively, the dose can be calculated relative to the body weight of the patient. In this event, a typical dose of pharmaceutical agent would have to be adjusted e.g. in a range between 0.1 µg and 100 µg per kg body weight, preferably between 1 and 50 µg/kg. Furthermore, however, it is also possible to determine the dose on the basis of particular organs rather than the whole patient. For example, this would be the case when placing the pharmaceutical agent according to the invention, e.g. in a biopolymer incorporated in the respective patient, near specific organs by means of surgery. Several biopolymers capable of liberating peptides or recombinant proteins in a desirable manner are known to those skilled in the art. For example, such a gel may include 1 to 1000 µg of the pharmaceutical composition of the invention, e.g. peptides or recombinant proteins, or of pharmaceutical agent per ml gel composition, preferably between 5 and 500 µg/ml, and more preferably between 10 and 100 mg/ml. In this event, the therapeutic agent is administered as a solid, gel-like or liquid composition.

In another preferred embodiment of the invention, the carriers are selected from the group of fillers, diluents, binders, humectants, disintegrants, dissolution retarders, absorption enhancers, wetting agents, adsorbents and/or lubricants.

The fillers and diluents are preferably starches, lactose, cane-sugar, glucose, mannitol and silica, the binder is preferably carboxymethylcellulose, alginate, gelatin, polyvinylpyrrolidone, the humectant is preferably glycerol, the disintegrant is preferably agar, calcium carbonate and sodium carbonate, the dissolution retarder is preferably paraffin, and the absorption enhancer is preferably a quaternary ammonium compound, the wetting agent is preferably cetyl alcohol and glycerol monostearate, the adsorbent is preferably kaolin and bentonite, and the lubricant is preferably talc, calcium and magnesium stearate, a solid polyethylene glycol or concerns mixtures of the materials mentioned above.

In another preferred embodiment of the invention the inventive compounds are prepared as gel, poudrage, powder, tablet, sustained-release tablet, premix, emulsion, brew-up formulation, drops, concentrate, granulate, syrup, pellet, bolus, capsule, aerosol, spray and/or inhalant and/or inhalant and/or applied in this form. The tablets, coated tablets, capsules, pills and granulates can be provided with conventional coatings and envelopes optionally including opacification agents, and can be composed such that release of the active substance(s) takes place only or preferably in a particular part of the intestinal tract, optionally in a delayed fashion, to which end polymer substances and waxes can be used as embedding materials.

For example, the drugs of the present invention can be used in oral administration in any orally tolerable dosage form, including capsules, tablets and aqueous suspensions and solutions, without being restricted thereto, however. In case of tablets for oral application, carriers frequently used include lactose and corn starch. Lubricants such as magnesium stearate are typically added. For oral administration in the form of capsules, useful diluents include lactose and dried corn starch. In oral administration of aqueous suspensions the active substance is combined with emulsifiers and suspending agents. Also, particular sweeteners and/or flavors and/or coloring agents can be added, if desired.

The active substance(s), i.e., the compounds of the invention, optionally can be present in a micro-encapsulated form, together with one or more of the above-mentioned carrier substances.

In addition to the active substance(s), suppositories may include conventional water-soluble or water-insoluble carrier substances, e.g. polyethylene glycols, fats, e.g. cocoa fat and higher esters (for example, $C_{14}$ alcohol with $C_{16}$ fatty acid) or mixtures of such materials.

In addition to the active substance(s), ointments, pastes, creams and gels may include conventional carrier substances, e.g. animal and vegetable fats, waxes, paraffins, starch, tragacanth, cellulose derivatives, polyethylene glycols, silicones, bentonites, silica, talc and zinc oxide or mixtures of these materials.

In addition to the active substance(s), powders and sprays may include conventional carriers such as lactose, talc, silica, aluminum hydroxide, calcium silicate and polyamide powder or mixtures of these substances. In addition, sprays may include conventional propellants such as chlorofluoro-hydrocarbons.

In addition to the active substance(s), solutions and emulsions may include conventional carriers such as solvents, solubilizers, and emulsifiers, e.g. water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, peanut oil, corn oil, olive oil, castor oil and sesame oil, glycerol, glycerol formal, tetrahydrofurfuryl alcohol, polyethylene glycols, and fatty esters of sorbitan, or mixtures of these substances. For parenteral application, the solutions and emulsions may also be present in a sterile and blood-isotonic form.

In addition to the active substance(s), suspensions may include conventional carriers such as liquid diluents, e.g. water, ethyl alcohol, propylene glycol, suspending agents, e.g. ethoxylated isostearyl alcohols, polyoxyethylene sorbitol and sorbitan esters, microcrystalline cellulose, aluminum metahydroxide, bentonite, agar, tragacanth, or mixtures of these substances.

The drugs can be present in the form of a lyophilized sterile injectable formulation, e.g. as a sterile injectable aqueous or oily suspension. Such a suspension can also be formulated by means of methods known in the art, using suitable dispersing or wetting agents (such as Tween 80) and suspending agents. The sterile injectable formulation can also be a sterile injectable solution or suspension in a non-toxic, parenterally tolerable diluent or solvent, e.g. a solution in 1,3-butanediol. Tolerable vehicles and solvents that can be used include mannitol, water, Ringer's solution, and isotonic sodium chloride solution. Furthermore, sterile, non-volatile oils are conventionally used as solvents or suspending medium. Any mild non-volatile oil, including synthetic mono- or diglycerides, can be used for this purpose. Fatty acids such as oleic acid and glyceride derivatives thereof can be used in the production of injection agents, e.g. natural pharmaceutically tolerable oils such as olive oil or castor oil, especially in their polyoxyethylated forms. Such oil solutions or suspensions may also include a long-chain alcohol or a similar alcohol as diluent or dispersant.

The above-mentioned formulation forms may also include colorants, preservatives, as well as odor- and taste-improving additives, e.g. peppermint oil and eucalyptus oil, and sweeteners, e.g. saccharine. Preferably, the compounds according to the invention should be present in the above-mentioned pharmaceutical formulations at a concentration of about 0.1 to 99.5, more preferably about 0.5 to 95 wt.-% of the overall mixture.

In addition to the compounds of the invention, the above-mentioned pharmaceutical preparations may include further pharmaceutical active substances. The production of the pharmaceutical preparations specified above proceeds in a usual manner according to well-known methods, e.g. by mixing the active substance(s) with the carrier substance(s).

The above-mentioned preparations can be applied orally, nasally, rectally, regionally, e.g. liver, spleen, kidneys, lungs or the like, parenterally (intravenous, intramuscular, subcutaneous routes), intracisternally, intravaginally, intraperitoneally, locally (powder, ointment, drops) in humans and animals and used in the therapy of inflammations or cancer in hollow areas and body cavities. For oral therapy, injection solutions, solutions and suspensions, gels, brew-up formulations, emulsions, ointments or drops are possible as suitable preparations. For local therapy, ophthalmic and dermatological formulations, silver and other salts, ear drops, eye ointments, powders or solutions can be used. With animals, ingestion can be effected via feed or drinking water in suitable formulations. Furthermore, gels, poudrage, powders, tablets, sustained-release tablets, premixes, concentrates, granulates, pellets, boli, capsules, aerosols, sprays and inhalants can be used in humans and animals. Furthermore, the compounds of the invention can be incorporated in other carrier materials such as plastics (plastic chains for local therapy), collagen or bone cement.

In another preferred embodiment of the invention the compounds according to the invention are incorporated in a formulation at a concentration of 0.1 to 99.5, preferably 0.5 to 95, and more preferably 20 to 80 wt.-%. That is, the compounds of the invention are present in the above-specified pharmaceutical formulations, e.g. tablets, pills, granulates and others, at a concentration of preferably 0.1 to 99.5 wt.-% of the overall mixture. The amount of active substance, i.e., the amount of a compound according to the invention that is combined with the carrier materials to produce a single dosage form, can be varied by a person skilled in the art depending on the host to be treated, the tumor to be treated, and on the particular type of administration. Once the condition of a host or patient has improved, the proportion of active compound in the preparation can be modified so as to obtain a maintenance dose. Depending on the symptoms, the dose or frequency of administration or both can subsequently be reduced to a level where the improved condition is retained. Once the symptoms have been alleviated to the desired level, the treatment should be stopped. However, patients may require an intermittent treatment on a long-term basis if any symptoms of the disease should recur. Accordingly, the proportion of the compounds, i.e. their concentration, in the overall mixture of the pharmaceutical preparation, as well as the composition or combination thereof, is variable and can be modified or adapted by a person of specialized knowledge in the art.

Those skilled in the art will be aware of the fact that the compounds of the invention can be contacted with an organism, preferably a human or an animal, on various routes. Furthermore, a person skilled in the art will also be familiar with the fact that the pharmaceutical agents in particular can be applied at varying dosages. Application should be effected in such a way that a tumor is combatted as effectively as possible, or the onset of such a disease is prevented by a prophylactic administration. Concentration and type of application can be determined by a person skilled in the art using routine tests. Preferred applications of the compounds of the invention are oral application in the form of powder, tablets, fluid mixtures, drops, capsules or the like, rectal application in the form of suppositories, solutions and the like, parenteral application in the form of injections, infusions and solutions, inhalation of vapors and aerosols, powders and pads, and local application in the form of ointments, pads, dressings, lavages and the like. Contacting with the compounds according to the invention is preferably effected in a prophylactic or therapeutic fashion. In prophylactic administration, development of the specified tumors is to be prevented at least in such a way that further propagation thereof is massively reduced, or that tumors are almost completely eliminated. In therapeutic contacting, a manifest tumor disease of a patient is already existing, and the and tumors already existing in the body should be either destroyed or inhibited in their propagation. Other forms of application preferred for this purpose are e.g. subcutaneous, sublingual, intravenous, intramuscular, intraperitoneal and/or topical ones.

In addition to the above-specified concentrations during use of the compounds of the invention, the compounds in a preferred embodiment can be employed in a total amount of 0.05 to 500 mg/kg body weight per 24 hours, preferably 5 to 100 mg/kg body weight. Advantageously, this is a therapeutic quantity which is used to prevent or improve the symptoms of a disorder or of a responsive, pathologically physiological condition. The amount administered is sufficient to inhibit tumor growth.

Obviously, the dose will depend on the age, health and weight of the recipient, degree of the disease, type of required simultaneous treatment, frequency of the treatment and type of the desired effects, and side-effects. The daily dose of 0.05 to 500 mg/kg body weight can be applied as a single dose or multiple doses in order to furnish the desired results. The dosage levels per day are applicable both in prophylaxis and treatment of a tumor disease, including infection, e.g. infections inducing or co-inducing a tumor, such as hepatitis, especially hepatitis B infection. In particular, pharmaceutical agents are typically used in about 1 to 7 administrations per day, or alternatively or additionally as a continuous infusion. Such administrations can be applied as a chronic or acute therapy. Of course, the amounts of active substance that are combined with the carrier materials to produce a single dosage form may vary depending on the host to be treated and on the particular type of administration. In a preferred fashion, the daily dose is distributed over 2 to 5 applications, with 1 to 2 tablets including an active substance content of 0.05 to 500 mg/kg body weight being administered in each application. Of course, it is also possible to select a higher content of active substance, e.g. up to a concentration of 5000 mg/kg. The tablets can also be sustained-release tablets, in which case the number of applications per day is reduced to 1 to 3. The active substance content of sustained-release tablets can be from 3 to 3000 mg. If the active substance—as set forth above—is administered by injection, the host is preferably contacted 1 to 8 times per day with the compounds of the invention or by using continuous infusion, in which case quantities of from 1 to 4000 mg per day are preferred. The preferred total amounts per day were found advantageous both in human and veterinary medicine. It may become necessary to deviate from the above-mentioned dosages, and this depends on the nature and body weight of the host to be treated, the type and severity of the disease, the type of formulation and application of the drug, and on the time period or interval during which the administration takes place. Thus, it may be preferred in some cases to contact the organism with less than the amounts mentioned above, while in other cases the amount of active substance specified above has to be surpassed. A person of specialized knowledge in the art can easily determine the optimum dosages required in each case and the type of application of the active substances.

In another particularly preferred embodiment of the invention the compounds of the invention are used in a single administration of from 1 to 80, especially from 3 to 30 mg/kg body weight. In the same way as the total amount per day, the amount of a single dose per application can be varied by a person of specialized knowledge in the art. Similarly, the compounds used according to the invention can be employed in veterinary medicine with the above-mentioned single concentrations and formulations together with the feed or feed formulations or drinking water. A single dose preferably includes that amount of active substance which is administered in one application and which normally corresponds to one whole, one half daily dose or one third or one quarter of a daily dose. Accordingly, the dosage units may preferably include 1, 2, 3 or 4 or more single doses or 0.5, 0.3 or 0.25 single doses. In a preferred fashion, the daily dose of the compounds according to the invention is distributed over 2 to 10 applications, preferably 2 to 7, and more preferably 3 to 5 applications. Of course, continuous infusion of the agents according to the invention is also possible.

In a particularly preferred embodiment of the invention, 1 to 10 tablets or capsules, preferably 4 to 8 capsules or tablets, and more preferably 6 capsules or tablets are administered in each oral application of the compounds of the invention. The tablets according to the invention can be provided with coatings and envelopes well-known to those skilled in the art or can be composed in a way so as to release the active substance(s) only in preferred, particular regions of the host.

In another preferred embodiment of the invention the compounds according to the invention can be employed together with at least one other well-known pharmaceutical agent. That is to say, the compounds of the invention can be used in a prophylactic or therapeutic combination in connection with well-known drugs. Such combinations can be administered together, e.g. in an integrated pharmaceutical formulation, or separately, e.g. in the form of a combination of tablets, injection or other medications administered simultaneously or at different times, with the aim of achieving the desired prophylactic or therapeutic effect. These well-known agents can be agents which enhance the effect of the compounds according to the invention.

Of course, it is also possible to use the compounds of the invention, particularly the pharmaceutical agents, alone or together with other agents in a therapy, e.g. in a combination therapy, as a regional therapy; this can be preferred in the event of a liver tumor, for example.

It is well-known to those skilled in the art that increasing the concentration of agents oxidizing glutathione or increasing the inactivation of glutathione can be advantageous in particular tumor diseases. For example, DL-buthionine-(SR)-sulfoximine can be used for glutathione depletion.

Typically, there is an optimum ratio of compound(s) of the invention with respect to each other and/or with respect to other therapeutic or effect-enhancing agents (such as transport inhibitors, metabolic inhibitors, inhibitors of renal excretion or glucuronidation, such as probenecid, acetaminophen, aspirin, lorazepan, cimetidine, ranitidine, colifibrate, indomethacin, ketoprofen, naproxen etc.) where the active substances are present at an optimum ratio. Optimum ratio is defined as the ratio of compound(s) of the invention to other therapeutic agent(s) where the overall therapeutic effect is greater than the sum of the effects of the individual therapeutic agents. In general, the optimum ratio is found when the agents are present at a ratio of from 10:1 to 1:10, from 20:1 to 1:20, from 100:1 to 1:100 and from 500:1 to 1:500. In some cases, an exceedingly small amount of a therapeutic agent will be sufficient to increase the effect of one or more other agents. In addition, the use of the compounds of the invention in combinations is particularly beneficial in order to reduce the risk of developing resistance and/or increase the therapeutic effectiveness. Of course, the compounds of the invention can be used in combination with other well-known anti-tumor agents. Such agents are well-known to those skilled in the art. Accordingly, the compounds of the invention can be administered together with all conventional agents, especially other drugs, available for use particularly in connection with tumor drugs, either as a single drug or in a combination of drugs. They can be administered alone or in combination with same.

In a preferred fashion the compounds of the invention are administered together with said other well-known pharmaceutical agents at a ratio of about 0.005 to 1. Preferably, the compounds of the invention are administered particularly together with virus-inhibiting agents at a ratio of from 0.05 to about 0.5 parts and up to about 1 part of said known agents. The pharmaceutical composition can be present in substance or as an aqueous solution together with other materials such as preservatives, buffer substances, agents to adjust the osmolarity of the solution, and so forth.

In a preferred fashion the pharmaceutical agent is employed as a vaccine after tumor formation, or as a preventive vaccination. Advantageously, vaccination is effected in such a way that, following application, a protection against spreading or formation of tumors is developed in the organism. Of course, it is also possible to effect vaccination immediately prior to or shortly after manifestation of a tumor, or as a therapy with a plurality of applications. Those skilled in the art are familiar with the fact that tumor treatment can be advantageous at virtually any point in time following formation of metastases, so that vaccination in the meaning of the invention could also be application of the inventive pharmaceutical agent weeks, months, years or decades after formation of a tumor.

The invention also relates to a kit and to the use thereof in medicine. In a preferred fashion, the compounds of the invention or the kit comprising same are used in a combination therapy, especially in the treatment of tumors. In a particularly preferred fashion, said combination therapy comprises a chemotherapy, a treatment with cytostatic agents and/or a radiotherapy. In a particularly preferred embodiment of the invention the combination therapy is an adjuvant, biologically specific form of therapy, and in a particularly preferred fashion, said form of therapy is an immune therapy. Furthermore, in a particularly preferred fashion the combination therapy comprises a gene therapy and/or a therapy using a compound according to the invention. Various combination therapies, especially for the treatment of tumors, are well-known to those skilled in the art. For example, a treatment with cytostatic agents or e.g. irradiation of a particular tumor area can be envisaged within the scope of a combination therapy, and this treatment is combined with a gene therapy, using the compounds of the invention as anticancer agents. Accordingly, the use of the compounds according to the invention for increasing the sensitivity of tumor cells to cytostatic agents and/or radiation can be particularly preferred. Furthermore, a preferred use of the compounds according to the invention is in inhibiting the vitality, the proliferation rate of cells and/or inducing apoptosis and cell cycle arrest.

In a preferred embodiment the cancerous disease or tumor being treated or prevented is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Ley-dig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangio-endothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor being treated or prevented is selected from the group of tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarian carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, morbus Hodgkin, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancy such as Kaposi sarcoma, AIDS-associated lymphomas, AIDS-associated lymphomas of the central nervous system, AIDS-associated morbus Hodgkin and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor being treated or prevented is selected from the group comprising mammary carcinomas, gastrointestinal tumors, including colon carcinomas, stomach carcinomas, pancreas carcinomas, colon cancer, small intestine cancer, ovarian carcinomas, cervical carcinomas, lung cancer, prostate cancer, kidney cell carcinomas and/or liver metastases.

Without intending to be limiting, the invention will be explained in more detail with reference to the following examples.

DESCRIPTION OF VARIOUS AND PREFERRED EMBODIMENTS OF THE INVENTION

1. Synthesis of cis-diammoniumdichlorodihydroxoplatinum (IV)

150 g of cisplatin is suspended in about 300 ml of water in a 2 liter three-necked flask (provided with precision glass stirrer) and added with 350 ml $H_2O_2$ (35%) in portions with stirring over a period of 2 days. Stirring is continued for another 4 days at about 20° C. Thereafter, the raw product is sucked off, washed with a small amount of ice water, dissolved in a precisely sufficient amount of 0.5 N sulfuric acid, and subsequently precipitated with 35% NaOH (pH ~7-8). After storage in a refrigerator overnight, the yellow crystalline mass is sucked off, washed with a small amount of cold water, ethanol and eventually with ether and dried in vacuum.

Yield (3 batches): 336.7 g (67.2% of theoretical)

2. Synthesis of cis-diammoniumdichlorodihydroxoplatinum (IV) Disodium Salt 20 g (0.06 mol) of cis-diammoniumdichlorodihydroxoplatinum(IV) is dissolved in about 450 ml of aqueous sodium hydroxide solution (containing 4.8 g (0.12 mol) of NaOH) with heating and, following cooling to room temperature, stored in a refrigerator overnight. The precipitated reaction product is sucked off, washed with a small amount of cold water, ethanol and eventually with ether and dried in vacuum.

Yield: 13.6 g (59.9% of theoretical)

3. Synthesis of cis-diammoniumdichlorodihydroxoplatinum (IV) Calcium Salt

Oxoplatin (9.3 g) is suspended in 80 ml of water and, following addition of an equimolar amount (2.1 g) of calcium hydroxide, stirred for 24 hours at room temperature. Thereafter, the reaction product is sucked off, washed with water, ethanol and ether and dried in vacuum.

Yield: 7.7 g.

4. Synthesis of Platinum(IV) Compounds Comprising Alkyl or Aryl Residues

The trans- or cis-diammoniumdichlorodihydroxoplatinum (IV) compounds (platinum(IV) hydroxo compounds) produced using the method according to the invention are largely inert and have such nucleophilicity to allow good reaction with weakly electrophilic reagents. The platinum(IV) hydroxo compounds are placed in an inert solvent (ether) and mixed by continuous stirring. In particular, stirring can be effected using an electric stirrer on typical laboratory stirring apparatus. The stirred solution is added with an excess of alkyl or aryl anhydrides, e.g. phenyl anhydrides (benzoic anhydrides). In addition to these anhydrides, it is possible to use the corresponding isocyanates and pyrocarbonates. The mixture is stirred for about 12 to 48 hours. If the selected platinum(IV) hydroxo compound is a sparingly soluble compound, the mixture is heated e.g. by switching on the hot-stage of the stirring apparatus during stirring. Also, the reaction can be improved by using a highly polar reaction medium. The reaction product precipitates upon cooling and can be filtrated off. Further standard purification steps are performed depending on the desired level of purity.

Thereafter, the resulting alkyl or aryl derivatives of the platinum(IV) hydroxo compounds can be tested for their tumor-inhibiting effect in laboratory animals. In the presence of ascorbates, it is possible to convert the platinum(IV) compounds into platinum(II) compounds over a period of several days. Accordingly, the compounds of the invention can also be regarded as prodrugs of platinum(II) compounds.

5. Use of cis-diammoniumdichlorodihydroxoplatinum(IV) and Salts Thereof

Growth inhibition tests on various human cell lines show the different activities of cisplatin, cis-oxoplatin and oxaliplatin. The results illustrated below show that cis-oxoplatin has an activity similar to that of oxaliplatin, but higher activity than carboplatin. The following Table illustrates the results produced with cisplatin, oxoplatin, carboplatin and oxaliplatin (the values specified are $IC_{50}$ values in μg/ml, i.e., the concentration where 50% of the cells survive, nd=not determined; res=resistant=non-sensitive or $IC_{50}$ value cannot be determined at a concentration of up to 40 μg/ml; IC=inhibition concentration).

TABLE 1

| Cell line | Cis-platin | cis-Oxoplatin | Carboplatin | Oxaliplatin |
|---|---|---|---|---|
| HOS Osteosarcoma | nd | 2.5 | 5 | nd |
| SaOS Osteosarcoma | nd | 5 | 5 | nd |
| PC3 Prostate | res | 7.5 | 10 | nd |
| M607 Melanoma | 0.3 | 5 | 10 | 10 |
| M518 Melanoma | 40 | res | res | res |
| Me128 Melanoma | 0.3 | 2.5 | 10 | 10 |
| JVSO Melanoma | 40 | 10 | res | res |
| Panc1 Pancreatic cancer | 1 | 40 | 20 | 5 |
| BxPC3 Pancreatic cancer | 0.6 | 2.5 | 10 | 10 |

TABLE 1-continued

| Cell line | Cis-platin | cis-Oxoplatin | Carboplatin | Oxaliplatin |
|---|---|---|---|---|
| MiaPaCa2 Pancreatic cancer | 1.5 | 5 | 5 | 5 |
| HCT8 Colon carcinoma | 5 | 40 | res | res |
| HT29 Colon carcinoma | 0.3 | 20 | 20 | 20 |
| HCT-15 Colon carcinoma | 0.3 | 20 | res | 10 |
| A498 Renal cells | 1 | 20 | res | 10 |
| C320DM Colon carcinoma | 0.3 | 2.5 | 10 | 0.15 |
| Colo205 Colon carcinoma | 10 | res | res | 1 |
| CC1227 Colon carcinoma | 0.3 | 10 | res | 0.2 |
| MCF-7 Breast cancer | 2.5 | 5.5 | res | res |
| T47D Breast cancer | 0.3 | 2.5 | nd | 0.1 |

TABLE 2

| | $IC_{50}$ μg/ml | |
|---|---|---|
| Cell line | cis-Oxoplatin | cis-Oxoplatin sodium salt |
| T47D Breast cancer | 3 | 18 |
| SK-OV3 Ovarian cancer | 15 | 22 |
| U 373 MG Astrocytoma | 15 | 18 |
| BxPC3 Pancreatic carcinoma | 13 | 12 |
| SK-OV4 Ovarian cancer | 16.2 | 12.8 |
| PC3 Prostate | 7.5 | 5.3 |
| CaCo-2 Colon | 1.52 | 2.22 |
| CRO2B Carcinoid | 3.0 | 10.1 |
| HT29 Colon | 13.5 | 4.55 |
| Du145 Prostate | 19.0 | 27.0 |
| SW480 Colon | 8.2 | 2.5 |
| SIM Sarcoma | 15.2 | 11.2 |

The activities differ according to the cell line. The Na salt is clearly more effective (about 70%) with HT29 and SW480 and more effective with SK-OV4, PC3 and SIM (about 30%), and less efficient with CaCO-2, DU145 and CRO2B cells. The $IC_{50}$ values of these cells are therefore 10.5±6.4 μg/ml for oxoplatin versus 9.5±8 μg/ml for the sodium salt.

The following comparison shows the dose-response dependence for cis-oxoplatin versus cis-oxoplatin Na in PC3 cells:

| Conc. (μg/ml) | % Survival/oxoplatin | % Survival/Na salt |
|---|---|---|
| 40 | 15.8 ± 2.7 | 0.6 ± 0.5 |
| 20 | 56.7 ± 6.3 | 33.2 ± 3.0 |

-continued

| Conc. (μg/ml) | % Survival/oxoplatin | % Survival/Na salt |
|---|---|---|
| 10 | 87.4 ± 11.8 | 77.7 ± 2.4 |
| 5 | 105.2 ± 10.8 | 109.3 ± 9.1 |

These are typical results for PC3, SK-OV4 and SIM. The Na salt is more active at higher concentration ranges; the differences are smaller at lower concentrations. Presumably, cis-oxoplatin Na has a slightly different structure or a different mechanism of action compared to oxoplatin, so that it is 30 to 70% more active or 40 to 50% less active than cis-oxoplatin in particular cell lines. The superior activity of cis-oxoplatin Na appears to be present at higher concentration ranges (above 5 μg/ml).

Effect of cis-oxoplatin on Cell Lines of Typical Tumors in Children

What is seen primarily in children are leukemias, neuroblastomas and Ewing's sarcoma/peripheral neuroectodermal tumors (group of the Ewing family of tumors=EFT). The investigated tumor cell lines include three EFTs (EW-7, SIM and KAL), as well as two neuroblastoma cell lines (NB: LAN1 and LAN5; Los Angeles neuroblastoma=LAN) (see Table 3).

TABLE 3

| Cell line | Oxoplatin ($IC_{50}$ in μg/ml) |
|---|---|
| EW-7 (EFT) | 1.25 |
| SIM (EFT) | 14 |
| KAL (EFT) | not tested |
| LAN1 (NB) | 17 |
| LAN5 (NB) | 3.5 |

Comparison of the effect of cis-oxoplatin and cis-oxoplatin Ca

The effect of cis-oxoplatin Ca and cis-oxoplatin was compared on 10 cell lines (Table 4).

($IC_{50}$ values specified in μg/ml; the test was performed as a formazan test).

TABLE 4

| Cell line | Origin | Oxoplatin $IC_{50}$ (μg/ml) | Oxoplatin Ca $IC_{50}$ (μg/ml) |
|---|---|---|---|
| SW480 | Colon | 8.2 | 2.5 |
| MDA-MB-435 | Breast | 16.5 | 12.0 |
| BT20 | Breast | 3.75 | 3.5 |
| Colo205 | Colon | 29.0 | 13.5 |
| Du145 | Prostate | 19.0 | 14.5 |
| HT29 | Colon | 13.5 | 8.0 |
| CRO2B | Carcinoid | 3.0 | 2.20 |
| CaCo-2 | Colon | 1.52 | 0.87 |
| BxPC3 | Pancreas | 26.0 | 30.0 |
| T47D | Breast | 2.5 | 3.6 |

The $IC_{50}$ (±SEM) mean value of cis-oxoplatin for all cell lines is 12.3±3.2, compared to cis-oxoplatin Ca with an $IC_{50}$ value (±SEM) of 9.1±2.8.

The results determined show that chemically highly similar platinum compounds such as cisplatin and cis-oxoplatin have different effects on various human cancer cells, and that the salts of the platinum compounds show a behavior on tumors which is different from that of the base compounds from which the salts have been generated. In general, and extending beyond concrete tests, it appears that the DNA binding ability of cis-oxoplatin salts, especially of cis-oxoplatin sodium salt, is unexpected when compared to cis-oxoplatin. For example, this may have its cause in the different structures of the DNA adducts formed with the base, on the one hand, and with the salt, on the other hand. Furthermore, it can be assumed that the cis-oxoplatin salts undergo a different process of biotransformation compared to the corresponding bases. These unexpected variations are of great importance when using bases and salts in tumor therapy. For example, further important issues of such different behavior of bases and salts are: absorption, diffusion and distribution in the tissue and in particular organs. The intracellular uptake and the toxicity of cis-oxoplatin sodium salts are different from those of the corresponding base; the absorption and dissolution, as well as the pharmacogenetics of cis-oxoplatin salts are not comparable to those of the base. The type of interaction with DNA, and the efficiency and effectiveness, as well as the therapeutic potency of cis-oxoplatin salts are different from those of cis-oxoplatin. Inter alia, this can be demonstrated on the chemical structure of cis-oxoplatin calcium salt as one example of salts of bivalent cations:

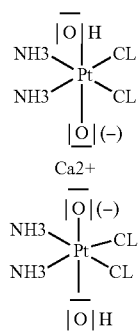

As can be seen in this structure, salts such as calcium salts have a structure that is completely different from that of the corresponding base. Such variations in the stereochemical properties result in a different behavior with respect to the interaction with DNA in cells, especially in cancer cells. As a result of the different structure of salts, a lower dose can be sufficient to achieve a therapeutic effect. Furthermore, biotransformation may result in conversion of platinum(IV) complexes into platinum(II) complexes in the body, and platinum(IV) and platinum(II) complexes have different effects on different tumors (see Table 1).

6. Cytotoxic Activity of Trans-oxoplatin (TRAXO)

trans-Oxoplatin was tested on a panel of cell lines, using double steps and an initial concentration of 40 μg/ml. As the $IC_{50}$ values were not reached in most cases, cell survival at the highest concentration is indicated.

TABLE 5

| Cell line | | % Survival with 40 μg/ml TRAXO (unless 20 μg/ml indicated) |
|---|---|---|
| U-87-MG | Astrocytoma | 100 |
| ASTRO | Astrocytoma | 82(20)/71 |
| SW620 | Colon carcinoma | 43/51/97 |
| MDA-MB-231 | Breast cancer | 70/103/106 |
| G-292 | Osteosarcoma | 8.6/68 |
| PANC1 | Pancreatic cancer | 100 |
| CRO1A | Carcinoid | 87/104/70 |

TABLE 5-continued

| Cell line | | % Survival with 40 µg/ml TRAXO (unless 20 µg/ml indicated) |
|---|---|---|
| CRO2B | Carcinoid | 24/57 |
| MIAPaCa2 | Pancreatic Cancer | 92/83 |
| Fib3 | Fibroblasts | 91 |
| K562 | Leukemia | 97 |
| WI-38 | Embryonic lung fibroblasts | 21 |
| COLO 205 | Colon carcinoma | 109 |
| HCT-15 | Colon carcinoma | 100 |
| T-47D | breast cancer | 101 |
| HL-60 | Leukemia | 0.5 |
| HOS | Osteosarcoma | 4.3 |
| ACHN | Renal carcinoma | 48 |
| BxPC3 | Pancreatic carcinoma | 106 |

As shown by the tests on 19 cell lines, TRAXO has considerable activity against a colon carcinoma cell line (SW 620), against 2 osteosarcoma cell lines (G-292, HOS), against a renal carcinoma cell line (ACHN), a leukemia cell line (HL-60), and against an embryonic pulmonary fibroblast cell line (WI-38). Cell lines sensitive to cis-oxoplatin, such as T-47D and BxPC3, are non-sensitive to TRAXO. The salts of the trans-oxoplatin compounds may have a different therapeutic potential and different effectiveness against particular human cancer cells, cell lines and tumors.

7. Antitumor Effectiveness of Alkyl Derivatives

Ethyl, propyl, phenyl and naphthyl derivatives of the platinum(IV) hydroxo compounds were tested in tumor rats, in which tests the above-mentioned derivatives were introduced into the target organism by infusion, on the one hand, and—on the other hand—as an oral administration in the form of a feed admixture. Surprisingly, oral administration was particularly effective because the derivatives obtained have a low molecular weight, are essentially neutral, inert with respect to their kinetics, stable to acid, and lipophilic to some extent. The tested components show exceptional cytotoxicity and good oral antitumor activity in the rat models. The tumor effectiveness was established by determining the tumor weight in grams. In non-treated tumor rats, the tumors had a weight of 37 g on an average. When administering the infusion agent (dose: 5 mg/kg body weight), mean values of the tumors of 31 g were determined. In oral administration, a mean tumor weight of 24 g was measured. The tests surprisingly showed that tumor rats (Walker carcinoma) could be treated particularly effectively by oral administration of the alkyl or aryl derivatives. Due to the fluctuations between individual aryl and alkyl derivatives measured during the tumor suppression tests, no statements as to significant variations can be made as yet.

What is claimed is:

1. A method for the preparation of trans- or cis-diammoniumdichlorodihydroxoplatinum(IV) or derivatives thereof, wherein
   trans- or cis-diammoniumdichloroplatinum(II) is reacted with a solution comprising >30% peroxide at temperatures below 30° C., and
   the product obtained is dissolved in a mineral acid and subsequently precipitated with an alkaline solution.

2. A compound of general formula

(I)

wherein $X_1$, $X_2$=sodium, potassium, lithium ions, alkyl and/or aryl residues.

3. A pharmaceutical agent, comprising a compound according to claim 2, optionally together with a pharmaceutically tolerable carrier, adjuvant and/or vehicle.

4. The pharmaceutical agent according to claim 3, wherein the carriers are fillers, diluents, binders, humectants, disintegrants, dissolution retarders, absorption enhancers, wetting agents, adsorbents and/or lubricants.

5. The pharmaceutical agent according to claim 3, wherein the carriers are liposomes, siosomes and/or niosomes.

6. A kit comprising the compounds according to claim 2, optionally together with information for combining the contents of the kit.

7. A combination tumor therapy comprising
   administering the compound of claim 2 to a person in need of such therapy in a therapeutically effective amount, and
   subjecting said person to a second tumor treatment.

8. The combination therapy of claim 7, wherein said second tumor treatment is chemotherapy, a treatment with cytostatic agents and/or a radiotherapy.

9. A method for therapy, follow-up and aftercare of a disease associated with cell growth, cell differentiation and/or cell division comprising
   administering the compound of claim 2 to a person in need of such therapy, follow-up or aftercare for a disease associated with cell growth, cell differentiation and/or cell division in a therapeutically, follow-up or aftercare effective amount.

10. The method of claim 9, wherein said disease is a tumor.

11. The method of claim 9, wherein the compound is administered orally, vaginally, rectally, nasally, subcutaneously, intravenously, intramuscularly, intraperitoneally, regionally and/or topically.

12. The method of claim 10, wherein the compound is administered orally, vaginally, rectally, nasally, subcutaneously, intravenously, intramuscularly, intraperitoneally, regionally and/or topically.

13. A compound of general formula

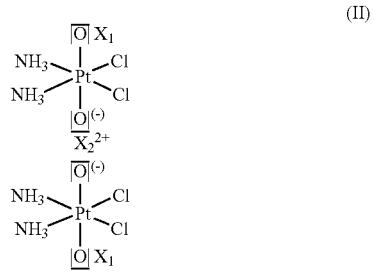

(II)

wherein $X_1$=sodium, potassium, lithium ions, alkyl and/or aryl residues, and
wherein $X_2$=calcium and/or magnesium.

14. A pharmaceutical agent, comprising a compound according to claim 13, optionally together with a pharmaceutically tolerable carrier, adjuvant and/or vehicle.

15. The pharmaceutical agent according to claim 14, wherein the carriers are fillers, diluents, binders, humectants, disintegrants, dissolution retarders, absorption enhancers, wetting agents, adsorbents and/or lubricants.

16. The pharmaceutical agent according to claim 14, wherein the carriers are liposomes, siosomes and/or niosomes.

17. A kit comprising the compounds according to claim 13, optionally together with information for combining the contents of the kit.

18. A combination tumor therapy comprising
administering the compound of claim 13 to a person in need of such therapy in a therapeutically effective amount, and
subjecting said person to a second tumor treatment.

19. The combination therapy of claim 18, wherein said second tumor treatment is chemotherapy, a treatment with cytostatic agents and/or a radiotherapy.

20. A method for therapy, follow-up and aftercare of a disease associated with cell growth, cell differentiation and/or cell division comprising
administering the compound of claim 13 to a person in need of such therapy, follow-up or aftercare for a disease associated with cell growth, cell differentiation and/or cell division in a therapeutically, follow-up or aftercare effective amount.

21. The method of claim 20, wherein said disease is a tumor.

22. The method of claim 20, wherein the compound is administered orally, vaginally, rectally, nasally, subcutaneously, intravenously, intramuscularly, intraperitoneally, regionally and/or topically.

23. The method of claim 21, wherein the compound is administered orally, vaginally, rectally, nasally, subcutaneously, intravenously, intramuscularly, intraperitoneally, regionally and/or topically.

* * * * *